United States Patent
Benson et al.

(10) Patent No.: US 9,603,526 B2
(45) Date of Patent: Mar. 28, 2017

(54) SYSTEMS AND METHODS FOR COMPOUND MOTOR ACTION POTENTIAL MONITORING WITH NEUROMODULATION OF THE PELVIS AND OTHER BODY REGIONS

(71) Applicant: CMAP Technology, LLC, Alpharetta, GA (US)

(72) Inventors: Kevin D. Benson, Sioux Falls, SD (US); Vincent R. Lucente, Allentown, PA (US); John R. Miklos, Atlanta, GA (US)

(73) Assignee: CMAP Technology, LLC, Alpharetta, GA (US)

( * ) Notice: Subject to any disclaimer, the term of this patent is extended or adjusted under 35 U.S.C. 154(b) by 126 days.

(21) Appl. No.: 14/530,211

(22) Filed: Oct. 31, 2014

(65) Prior Publication Data
US 2015/0126894 A1    May 7, 2015

Related U.S. Application Data

(60) Provisional application No. 61/898,918, filed on Nov. 1, 2013.

(51) Int. Cl.
*A61B 5/00* (2006.01)
*G06F 19/00* (2011.01)
(Continued)

(52) U.S. Cl.
CPC ........ *A61B 5/0022* (2013.01); *A61B 5/04882* (2013.01); *A61B 5/4836* (2013.01);
(Continued)

(58) Field of Classification Search
CPC .................................................. A61B 5/0022
See application file for complete search history.

(56) References Cited

U.S. PATENT DOCUMENTS 3,628,538 A    12/1971    Vincent
6,334,068 B1    12/2001    Hacker
(Continued)

FOREIGN PATENT DOCUMENTS

WO    WO 2013067018 A3 *  8/2013    ......... A61B 5/04001

OTHER PUBLICATIONS

International Search Report and Written Opinion of PCT/US14/63660 dated Apr. 14, 2015.

*Primary Examiner* — Michael C Stout
*Assistant Examiner* — Nicholas E Kolderman
(74) *Attorney, Agent, or Firm* — Gregory L. Mayback

(57) ABSTRACT

An electromyography muscle sensing system including a sensor platform and a cloud-based data analysis and storage platform. The sensor platform has an electromyography muscle sensor having sensing electrodes and a signal processing circuit having a sensor output, an analog-to-digital converter having a digital output, a memory, a communications device, a display indicating a status and an indication of CMAP presence, a microcontroller maintaining a record of a current procedure, transmitting in real-time the record, determining if CMAP is being achieved, and displaying a status or indication of CMAP. The data analysis and storage platform has a database, organizes and stores the output data, maintains a history of each procedure, analyzes the output data and defines a successful CMAP outcome, predicts an outcome of the current procedure if the output data correlates with stored output data of a successful CMAP outcome, and real-time communicates the outcome of the current procedure.

38 Claims, 7 Drawing Sheets

(51) Int. Cl.
*A61B 5/0492* (2006.01)
*A61B 5/0488* (2006.01)
*A61N 1/36* (2006.01)

(52) U.S. Cl.
CPC ........... *A61B 5/0002* (2013.01); *A61B 5/0492* (2013.01); *A61N 1/36007* (2013.01); *G06F 19/322* (2013.01); *G06F 19/3406* (2013.01)

(56) References Cited

U.S. PATENT DOCUMENTS

| | | | |
|---|---|---|---|
| 7,216,001 | B2 | 5/2007 | Hacker et al. |
| 7,328,068 | B2 | 2/2008 | Spinelli et al. |
| 7,369,894 | B2 | 5/2008 | Gerber |
| 7,623,925 | B2 | 11/2009 | Grill et al. |
| 7,763,034 | B2 | 7/2010 | Siegel et al. |
| 8,666,503 | B2 | 3/2014 | Choi et al. |
| 8,706,234 | B2 | 4/2014 | Sharma |
| 2003/0093006 | A1 | 5/2003 | Wells |
| 2005/0085743 | A1 | 4/2005 | Hacker |
| 2006/0276702 | A1 | 12/2006 | McGinnis |
| 2007/0060984 | A1 | 3/2007 | Webb |
| 2007/0282217 | A1 | 12/2007 | McGinnis |
| 2010/0262158 | A1 | 10/2010 | Siegel et al. |
| 2011/0237972 | A1 | 9/2011 | Garfield |
| 2012/0108999 | A1 | 5/2012 | Leininger |
| 2012/0143064 | A1 | 6/2012 | Cyphery |
| 2012/0197339 | A1 | 8/2012 | Takagi et al. |
| 2013/0079841 | A1 | 3/2013 | Su et al. |
| 2013/0158624 | A1 | 6/2013 | Bain et al. |
| 2013/0204097 | A1 | 8/2013 | Rodoni |
| 2013/0218229 | A1 | 8/2013 | Sharma |
| 2014/0031909 | A1 | 1/2014 | Ye et al. |
| 2014/0058283 | A1 | 2/2014 | Bartol et al. |
| 2014/0066950 | A1 | 3/2014 | MacDonald et al. |
| 2014/0107731 | A1 | 4/2014 | Stone et al. |
| 2014/0316484 | A1* | 10/2014 | Edgerton ........... A61N 1/36025 607/46 |

* cited by examiner

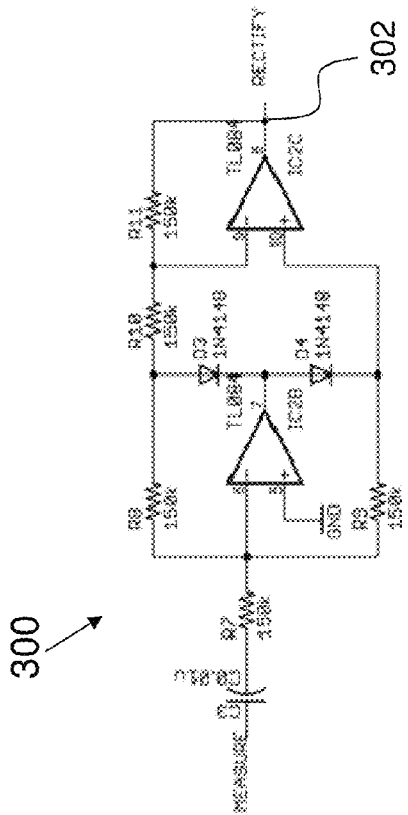
FIG. 1
FIG. 2
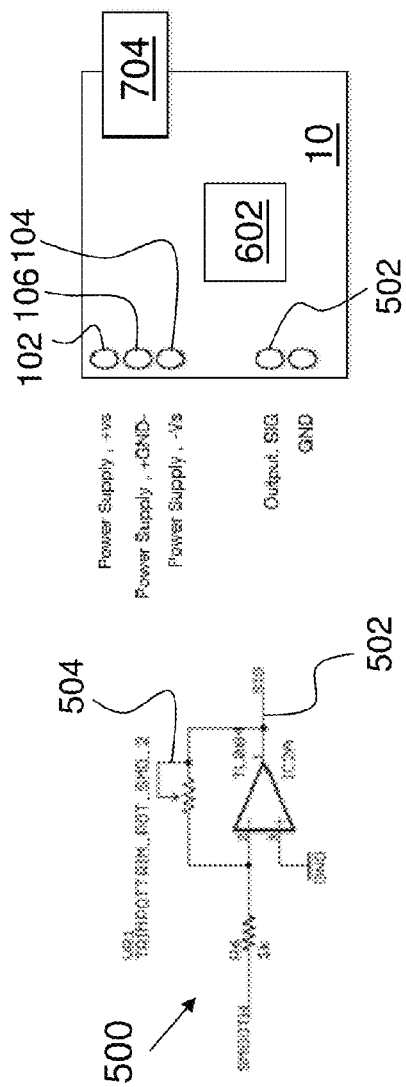
FIG. 3
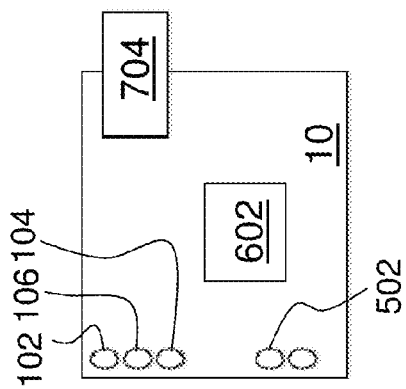
FIG. 4
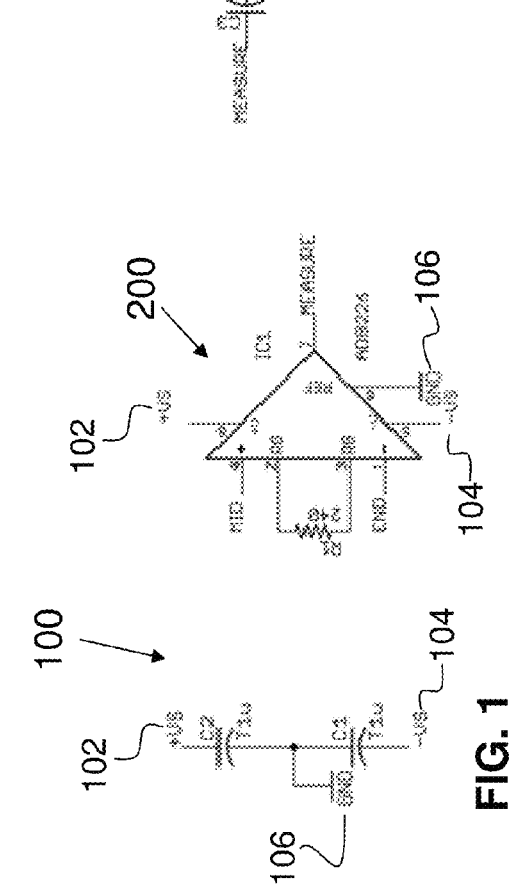
FIG. 5
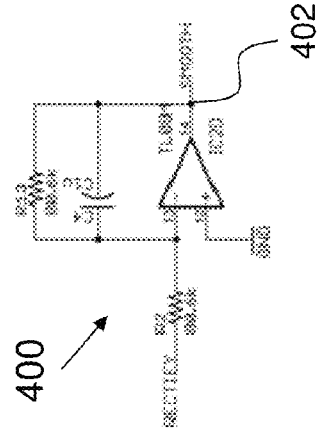
FIG. 6

SYSTEMS AND METHODS FOR COMPOUND MOTOR ACTION POTENTIAL MONITORING WITH NEUROMODULATION OF THE PELVIS AND OTHER BODY REGIONS

CROSS-REFERENCE TO RELATED APPLICATIONS

This application claims the priority, under 35 U.S.C. §119, of U.S. Provisional Patent Application No. 61/898,918, filed Nov. 1, 2013; the prior application is herewith incorporated by reference herein in its entirety.

STATEMENT REGARDING FEDERALLY SPONSORED RESEARCH OR DEVELOPMENT

Not Applicable

FIELD OF THE INVENTION

The present invention lies in the field of monitoring compound motor action potential for use with neuromodulation of the pelvis and other body regions.

BACKGROUND OF THE INVENTION

Dysfunction of the lower urinary tract and bowel systems affect nearly 100 million patients worldwide and, with a continued aging population, the incidence of these conditions will continue to grow. Medical science increasingly supports the primary theory for this dysfunction as an abnormal neurological communication between regulatory nervous system and the end organs (bladder, rectum, vagina, prostate etc. . . . ) being innervated. The regulatory nervous system, including the central nervous system (brain and spinal cord) and the peripheral nervous system, which system innervates the end organs and includes both afferent (sensory) and efferent (motor) divisions. Deterioration in the normal neuro-transmitted signals traveling up the afferent nerves carrying sensory feedback information as well as efferent motor axons signals traveling down the nerves toward their target tissues (most often muscle) can be precipitated by direct injury to the nerves, by an illness, or by aging. As a result, patients can develop various medical conditions to the end organs in the pelvis, i.e., the bladder and rectum, related to storage and elimination. Problems of storage as well as elimination of urine in the bladder can result in symptoms such as frequency, urgency (an overactive bladder), and incomplete bladder emptying. The rectum can have similar problems including fecal incontinence or chronic constipation.

Although first line therapies, such as diet or behavior therapy, and second line treatments, such as medications, can be helpful, many patients are simply non-compliant, see limited benefit, or suffer from intolerable side effects leading to discontinuation of their medical therapy. A third line therapy, neuromodulation, has been well-established as a safe and effective modality originally for refractory voiding dysfunctions and overactive bladder since 1997 and, more recently, since 2011, for fecal incontinence. Neuromodulation is the application of targeted electronic stimulus to modify primarily and directly afferent and efferent nerve signaling. Its direct application to the sacral and pudendal nerves in the pelvis and the posterior tibial nerves is quite effective for lower urinary tract and bowel dysfunction. Additional disorders involving the abdomen and pelvic organs, or muscle systems, such as Irritable Bowel Syndrome, interstitial cystitis, bowel motility disorders as well as chronic pelvic pain and sexual dysfunctions are being studied for potential benefit by neuromodulation. Neuromodulation has also been used safely and effectively to help relieve chronic back pain, pain from cancer and other nerve injuries, and pain from Complex Regional Pain Syndrome (CRPS) and Reflex Sympathetic Dystrophy (RSD), greatly improving the quality of life for patients. Presently, there are few treatments that can improve the activity level and the psychological outlook of a patient suffering from urinary or bowel dysfunction and/or pain disorders as well as neuromodulation techniques.

Neuromodulation presently involves a percutaneous procedure (although transvaginal or other natural orifice approaches are feasible) involving the placement of a needle to optimal proximity adjacent the desired nerve root, nerve, or branch, which then allows the physician to subsequently deliver a lead electrode introduced down the lumen of the needle. Proper or optimal positioning of the lead electrode within a very close proximity of the selected nerve is critical to achieve effective electrical stimulation, which promotes the desired clinical response. Currently, the delivery process is guided by fluoroscopic images of bony and soft tissue anatomical landmarks. Once fluoroscopic guidance has been achieved, electrical stimulation is employed to elicit motor and sensory responses from the patient to further refine or guide lead location.

Unfortunately there is a large margin of subjectivity to the interpretation of these "key" clinical responses. This includes both the patient's subjective assessment (i.e., feeling) and reporting (sensory response), and the implanting physician's subjective assessment when observing motor responses. Currently, physician measurement of response to neuromodulation stimulus is based on subjective markers such as a patient's perception of stimulation based on location of sensation and type of sensation. In the operating room, however, most patients are sedated or intubated. This leads to difficulty for patients to respond accurately to questions regarding sensation and location of stimulation. Not only does it require time for a patient to awaken to give feedback, medications adversely affect the patient's ability to respond accurately to questions, and there is a lack of clarity as to whether one's perception of appropriate stimulation is equated with actual stimulation efficacy. Objective measures of stimulation efficacy by the physician are based on a "bellows" response in the buttocks and dorsiflexion of the great toe. This, too, is open to subjective interpretation from the physician and it is unknown to what extent a patient may be able to exhibit these motor responses and the degree to which they need to be present to represent response.

As a result, despite what was thought at the time of implantation to be an optimal or "successful" lead placement, subsequent patient outcomes after lead deployment often does not correlate. In essence, with the current standard of care for performing neuromodulation, there is a poor correlation between the intra-operative method of evaluating electrode lead placement and postoperative optimal clinical success. The lack of consistent correlation between optimal intraoperative placement and postoperative clinical outcomes is an ongoing source of frustration for both patients and physicians. Suboptimal outcomes resulting in wasted healthcare dollars, despite what was thought to be a successful intraoperative placement, prevents a greater conversion of surgeons utilizing neuromodulation. A more specific and sensitive technique for optimal implantation would allow for greater postoperative patient success and ultimately greater acceptance and use among surgeons.

Compound muscle action potential (CMAP) or compound motor action potential is an electromyography investigation (i.e., an electrical study of muscle function). CMAP idealizes the summation of a group of almost simultaneous action potentials from several muscle fibers in the same area. These are usually evoked by stimulation of the motor nerve.

One common form of neuromodulation is referred to as InterStim therapy. Current forms of neuromodulation included sacral neuromodulation, pudendal neuromodulation, and posterior tibial nerve stimulation (Urgent PC).

Lower urinary tract complaints affect 1 in 3 adult women in the United States. Urinary urgency and urgency incontinence is a common form of urinary tract dysfunction. While not a cause of mortality, the morbidity of urinary urgency and urgency incontinence affects millions of women annually. Thirteen billion dollars was spent last year to control urinary incontinence. Many forms of therapy exist to help curb urinary urgency and incontinence. The American Urologic Association (AUA) has created an algorithm to manage these complaints. Simple cares are implemented initially including fluid management, avoidance of bladder irritants and urge suppression. If these fail, the next tier of treatment is medication. Two classes of medications are used, antimuscarinics and beta-3 agonists. Approximately 60% of patients may respond to the above two levels of treatment. However, side effects and limited efficacy limit the use of medications and compliance limits behavioral therapy. Many studies reveal that less than 20% of patients continue medical treatment beyond a few months and as many as 50% discontinue after a single month. The AUA recognizes a third tier of treatment for refractory symptoms. This level of care offers three choices, sacral neuromodulation (InterStim therapy), posterior tibial nerve stimulation (Urgent PC), and intradetrusor botulinum toxin A (Botox). Of these options, sacral neuromodulation is the only therapy recommended, as opposed to offered.

Sacral neuromodulation was developed in the 1980's and ultimately received FDA approval in 1997 for urinary urgency and urgency incontinence and was approved for non-obstructive urinary retention shortly thereafter. Over 150,000 InterStim implants have been placed since its inception and the therapy is growing logarithmically at this time, with over 50% of all implants placed in the last five years. Studies as well as multiple peer reviewed articles have shown excellent long term success using InterStim therapy. Sixty-five percent (65%) of urge incontinent patients are >50% improved over five years and over 60% of urinary retention patients are improved over five years.

InterStim therapy is a minimally invasive procedure that places a small electrode percutaneously in close proximity to the third sacral nerve root. This nerve level provides 80% of autonomic control to the bladder. A small needle A is placed next to the nerve root with the assistance of fluoroscopy (x-ray), as shown in FIG. 12. Based on the image and motor response (movement of the buttocks and great toe), the lead is placed temporarily for a two-week trial. During this time, the patient maintains a journal to document objective response to the test and, then, a decision is made to implant the lead under the skin for long term use. At this time, a generator (battery similar to a pacemaker) is placed under the skin in the buttock to operate the device for approximately five years. Of patients who currently trials the therapy, only about 60% go on to permanent implant. This is primarily due to lack of efficacy. Most experts feel this lack of efficacy is due to suboptimal lead placement at the time of the therapy trial.

The greatest limitation to optimal initial lead placement is the poor correlation between anatomical landmarks and actual neurophysiologic function. It has been believed that, if one places a lead and obtains motor responses and sensory coupling, then the lead is delivering effective therapy. Yet there has been no way to determine whether actual nerve stimulation is occurring. This may represent the single greatest reason why what seems to be an appropriate test fails.

One of the reasons why so many tests fail is the fact that current systems do not provide feedback indicating correct placement. FIG. 13 is a graph of a prior art monitoring device showing an example of a CMAP waveform as viewed by surgeons in the current state of the art. The electronic tracing curves on the display represent various depolarization and repolarization sets of the nerve being modulated through the electrode of FIG. 12. Each of the two dots B on each tracer curve is a "tracer spike," which is given off by the stimulating energy supplied to the nerve by the electrode lead of the neuromodulation device. Not only is it difficult to review the curves in real time, it is also difficult to determine the tracer spikes and, thereafter, to determine if the CMAP result is optimal, thus indicating optimal lead placement. As is apparent, the display screen of the prior art shown in FIG. 13 includes the ever-present "clutter" of a typical "overbuilt" prior art system. Such prior art systems require each user to visually interpret the series of electrical signals and make a subjective overall impression of what represents a true nerve response and, in doing so, attempt to determine if the signals displayed show that true nerve response or electrical interference or a signal artifact. It takes significant time and experience on the part of the user to "ferret out" such differences and, even with experience, there still exist areas of debate and judgment for each patient and each procedure. These disparities lead to variations in potential effectiveness of each surgery.

With traditional EMG devices, one will either use their own professional judgment or rely on a technologist for interpretation. The need for additional trained personnel limits the potential adaptation and widespread use of this prior art technology.

It would be beneficial if this problem could be overcome successfully, thus leading to a much higher implant rate and patient success. Based on theoretical models, a much higher rate of patients may be responders to InterStim therapy if the lead placement could be improved. This is also a great hindrance to both novice and experienced physicians using InterStim therapy.

In other areas of medicine and surgery, monitoring of nerve function is commonplace. Nerve conduction studies are invaluable to diagnose and treat many neurologic conditions. Intraoperative nerve conduction studies are the standard of care with most back and neck surgeries to determine if a nerve is compromised. From the experience of these fields, there is emerging data indicating that the technology can be very useful in optimizing InterStim therapy.

It would be beneficial to have objective measures for stimulation efficacy and accuracy that will lead to more uniform patient response to neuromodulation therapy. This could result in a greater number of patients responding to test therapy. Also, it would be beneficial to have greater device longevity from lower operational voltages. With such features, patient symptom resolution and satisfaction will increase. Lack of ongoing efficacy could be assessed and triaged, thus leading to more accurate and less frequent reprogramming and direct lead replacement when needed. This will lead to more uniform algorithms for programming and better assess when a replacement lead is needed.

Thus, a need exists to overcome the problems with the prior art systems, designs, and processes as discussed above.

SUMMARY OF THE INVENTION

Herein are provided systems and methods for compound motor action potential monitoring with neuromodulation of the pelvis and other body regions that overcome the hereinafore-mentioned disadvantages of the heretofore-known devices and methods of this general type and that provide such features with use of a process referred to as Compound Muscle Action Potential (CMAP) testing.

CMAP testing is a way to measure a loop of electrical conduction in a given nerve. Sensory nerve impulses are essential for the body to take in external data and process it, thus leading to a motor response (i.e., movement). The sensory arm of the reflex is referred to as the afferent limb and the motor response is referred to as the efferent limb. Central brain processing integrates the two limbs. CMAP technology allows one to see if sensory data is being integrated and results in an output of nervous system energy. An example of this is touching a hot stove, in which the sensory data is the hot coil and the motor response is the arm moving away quickly. In the case of sacral neuromodulation, the impulse is energy in a form arising from an external generator and the response is movement through the sacral and pudendal nerves. There needs to be a direct coupling of stimulus and effect to result in patient success. Use of CMAP technology allows one to actually see the resultant nerve conduction in direct response to the electrical stimulation of the nerve. It also allows one to visualize that the stimulus is not causing the resultant motor response. It is confirmation of this coupled reaction that appears to be critical to success of the therapy. Currently all that is available is a crude visual response (see FIG. 13) that may or may not actually be accurate.

In the systems and methods described herein, CMAP technology is integrated into current procedures. Two small perianal electrodes are placed to record the impulse and reflex "loop." A small grounding electrode is placed on the thigh. These electrodes are 27-gauge needles (smaller than a Tuberculin needle) and can be placed with the patient awake or sedated. The inventive systems replace the laptop-based model that are currently used, which systems are unnecessarily complex and are able to perform many tasks entirely unrelated to the issues being examined. The systems described herein utilize the same surgical procedure but arrive at results that are significantly more accurate than those procedures already being utilized.

The CMAP monitoring devices, systems, and processes utilize neuromodulation therapy for pelvic floor disorders including disorders of urination, defecation and pelvic floor muscle dysfunction. These monitoring systems and methods are capable of determining whether or not the stimulation-applying neuromodulation needle is appropriately placed and whether or not nerves that control pelvic floor function, urination, or defecation are being appropriately stimulated. The disclosed monitoring devices and methods can, therefore, help guide appropriate use of neuromodulation for pelvic floor disorders. The monitoring device is provided with at least one pair of recording electrodes and a grounding electrode that record a stimulation signal (due to neuromodulation) to sacral or pudendal nerve roots and a display showing the measurement result from the measurement unit. The monitoring device utilizes software that is created for both a monitor type system and a variety of other platforms including smart phone, I-pads, laptop computers and other delivery devices.

CMAP testing allows for evaluation of the integrity of the nerve, the muscle supplied by the nerve, and the integrity of the neuromuscular junction. Currently, CMAP testing is used to evaluate nerve damage while doing neurosurgical cases such as spinal fusion and discectomy. In such cases, a complex array of CMAP leads is placed to evaluate for any inadvertent nerve injury that may occur during these procedures. If a signal is noted during the procedure, this indicates a potential injury to the nerve and the physician is advised to redirect the dissection. The application of CMAP testing in these neurosurgical procedures is not to identify the correct site for lead placement for neuromodulation, but instead to inform the surgeons as to appropriate and inappropriate areas to carry out tissue dissection. In neurosurgical applications of CMAP testing, a nerve response is a finding that something bad has happened. In cases of CMAP testing of the present systems and methods, i.e., neuromodulation, a nerve response is a good result as the systems and methods seek to actively stimulate the nerve indicating a response. Therefore, the devices and methods described herein are, essentially, the "reverse" of standard CMAP testing. Once a surgeon identifies a good response with the herein-described systems and methods, that surgeon can more accurately place the leads for optimal neuromodulation.

To monitor a variety of levels of nerve roots during neurosurgery operations, CMAP devices have evolved into complex multichannel entities that require a trained technician to apply, monitor, and evaluate responses. Most physicians, aside from neurologists and neurosurgeons, are not familiar with these devices and find them intimidating and impractical for use in normal practice. The greatest limitation is the "foreignness" of nerve conduction tools and interpretation of studies. Most practicing Urologists and Gynecologists have no formal training in neurodiagnostics. Another limitation is the limited availability of easy to use tools. Most CMAP devices are complex and "overbuilt" as set forth above. The tools are designed for complex surgeries using multiple sensors and channels and require specialized training and a specialized operating room technician.

Anecdotally, it has been shown that patient's clinical outcomes are better when nerve responses are present and accurately noted during neuromodulation implant procedures. The systems and methods described herein create a user friendly, simple, single channel device that allows a non-neurologist/neurosurgeon or, similarly, a specially trained technician to apply, utilize, and interpret nerve conduction and response in a reproducible manner.

In an exemplary embodiment of a method, CMAP assists in monitoring nerve/clinical response to application of energy to treat or diagnosis disease states in the body, including but not limited to the nervous system of the:

1) pelvis, abdomen, and vagina including bladder and rectal dysfunction (including storage and voiding dysfunction), irritable bowel disorders, motility dysfunction, colonic inertia, gastric emptying disorders, nausea, vomiting, vaginal dysfunction, sexual dysfunction, chronic pelvic and vaginal and vulvar pain, and pelvic floor dysfunction;
2) lower and upper extremities in an attempt at maintaining muscular tone as well as recover sensory and supraspinal control of these extremities in patients with chronic quadriplegia, paraplegia, or hemiplegia;

3) lower back muscles in an attempt to control chronic muscle spasms and chronic back pain; and 4) head, face, and neck in an attempt to treat spasticity of neck muscles as well as headaches due to muscular tension and migraines.

CMAP also assists in monitoring nerve/clinical response to application of energy for cosmetic indications. Specifically, the technology described herein assists in the appropriate application of energy to the nervous system of the face to treat and prevent wrinkles as well as the nervous system to the buttocks and extremities to improve muscular tone.

CMAP is utilized, but is not limited to, percutaneous routes as described. It can also be utilized transcutaneously, endoscopically, laparoscopically, and via laparotomy to help implant various types of neuromodulators.

The systems and methods described herein simplify and help interpret these complex signals obtained while stimulating nerves during surgery. In an exemplary embodiment of an electromyography muscle sensing device, electrical stimulation with CMAP provides feedback to the user to help interpret nerve conduction response signals to a given stimuli applied through a variety of methods to modulate clinical disease states, currently used extensively with neuromodulation. The electromyography muscle-sensing device finds the "best targeted" response to stimuli. Essentially, all patients have a range of responses that can be elicited. The device gives a graded signal to the user when the best "targeted" response is noted. This is analogized to shooting at a target and hitting either the bull's-eye or the outer rings of the target. Every patient responds better to neuromodulation if the stimulation is in the bull's-eye. The user knows when the test stimulation is being placed closest to the nerve and a functional stimulation is achieved. The device is used by medical professionals across a variety of clinical settings including operating rooms, ambulatory surgery centers, medical offices, and field/home use. The device, as used herein, encompasses both a physical device, a variety of software (user) platforms, and methods for using the devices and platforms. The platforms for administration may include Internet based, smart phone/tablet (other future technology) applications, and integrated electronic medical recording and storage.

To augment efficiency and success of the electromyography muscle-sensing device, a secondary system is provided, for example, over the cloud, to analyze the output signal from the patient in real time and compare that signal with previous data contained within a database and from that patient and/or other patients. The systems and methods eliminate human judgment and use computer processing and computer "learning" along with an ever-expanding patient database to compare signals obtained in real-time to a reference standard and then provide instant feedback as to the validity of the signal seen. The key problem in using current technology is differentiating from true signal and artifact. Often many users are unable to separate the two, leading to improper diagnosis and poor results. Developing "fingerprints" through the inventive database helps to differentiate these issues prospectively. As a result, the systems and methods create a smooth depiction (as opposed to the rough tracing currently seen). Processing by, for example, "averaging" of the signals allows an easier reading with instant feedback.

Significant benefits are achieved with the systems and methods described herein using CMAP. With the present inventive systems and methods, close to 90% of patients have gone on to permanent implant and success, which is in comparison to a national average of 60%. In addition, operative room time has been cut by over 50%. Patients also need far less postoperative reprogramming and have a much greater feeling of success.

With the foregoing and other objects in view, there is provided, in accordance with the invention, an electromyography muscle sensing system including a sensor platform and a cloud-based data analysis and storage platform. The sensor platform has an electromyography muscle sensor having sensing electrodes with patient contacts at which electrical energy is at least one of measured and supplied and a signal processing circuit electrically connected to the sensing electrodes and having a sensor output, an analog-to-digital converter electrically connected to the sensor output and having a digital output at which is supplied a signal representing an electromyogram waveform, a memory, a communications device sending output data from the sensor platform and receiving input data into the sensor platform, a display displaying information to a user to indicate at least one of a status of the sensor platform and an indication of CMAP presence or absence, a microcontroller electrically connected to the sensor, the analog-to-digital converter, the memory, the display, and the communications device, the microcontroller receiving from the digital output the signal and storing at least a portion of the signal in the memory, maintaining a record of a current procedure being performed by the sensor platform, providing communication directives to the communications device to transmit in real-time at least portions of the record to and/or from the sensor platform, determining if CMAP is being achieved in the current procedure, and providing at the display at least one of the status of the sensor platform and the indication of CMAP presence or absence. The cloud-based data analysis and storage platform is communicatively connected at least to the communications device of the sensor platform to receive the output data from the sensor platform and to send the input data to the sensor platform. The cloud-based data analysis and storage platform has a database, centrally organizes and stores the output data from the sensor platform in the database, maintains a history of each procedure of the sensor platform in the database, analyzes the stored output data and the history to define stored output data of a successful CMAP outcome, predicts an outcome of the current procedure by comparing at least a portion of the output data in the current procedure with output data in the database to determine if the portion of the current output data correlates with the stored output data of the successful CMAP outcome, and communicates in real time the outcome of the current procedure.

In accordance with another feature of the invention, the sensor platform is a wireless handheld sensor platform.

In accordance with a further feature of the invention, the sensor platform is one of a laptop, a smart phone, and a tablet.

In accordance with an added feature of the invention, the sensor platform is a plurality of sensor platforms.

In accordance with an additional feature of the invention, the sensing electrodes comprise a positive electrode, a negative electrode, and a ground electrode.

In accordance with yet another feature of the invention, the signal processing circuit includes an amplification circuit having an input connected to at least one of the electrodes and a first amplification output, a rectification circuit connected to the first amplification output of the amplification circuit having a rectified output at which is provided a rectified signal, a smoothing circuit connected to the rectified output, smoothing the rectified signal, and having a smoothed output, and a publication circuit amplifying the smoothed output and publishing the output signal.

In accordance with yet a further feature of the invention, a voltage of the output signal supplied to the an analog-to-digital converter represents.

In accordance with yet an added feature of the invention, the signal includes values of at least one of date, time, and session identifier and the microcontroller stores the values in the memory.

In accordance with yet an additional feature of the invention, the communications device is a wireless radio, in particular, a Bluetooth radio.

In accordance with again another feature of the invention, the signal processing circuit includes at least one of a filter having settings for gain, high cut, and low cut, a trigger threshold sensitivity, a time base with a trigger window, and a selective audio filter.

In accordance with again a further feature of the invention, the user and default settings of the sensor include at least one of voltage, signal gain, sample frequency, and amplitude.

In accordance with again an added feature of the invention, records of the current procedure include a patient's demographic information, a procedure duration, and EMG event data.

In accordance with again an additional feature of the invention, CMAP is achieved according to the formula Delta EMG=ABS(E1–E2), where a time between E1 and E2 is in milliseconds and EMG is a value of the digital output.

In accordance with still another feature of the invention, the graphical mapping can be indicated at the display by at least one of sound, lights, graphics, and tactile measures.

In accordance with still a further feature of the invention, the cloud platform is a centralized computer server connected to the Internet.

In accordance with still an added feature of the invention, the cloud platform stores data stored securely to comply with health information privacy laws.

In accordance with still an additional feature of the invention, the microcontroller is programmed to: receive from the digital output the signal at a sampling rate frequency and store the sampled digital output in the memory, control user and default settings of the sensor, record the settings in the memory for each procedure conducted by the user of the sensor platform, and map a value of the sensor output and communicate to the user whether or not CMAP is being achieved.

In accordance with a further feature of the invention, every time a CMAP procedure is undertaken with the sensor platform, the cloud-based data analysis and storage platform stores the output data in the database and asks the user to tag that data as achieving one of a successful CMAP and an unsuccessful CMAP.

In accordance with a concomitant feature of the invention, the cloud-based data analysis and storage platform authenticates and authorizes use of the sensor platform and, upon authorization, records demographic information of the patient, identifies candidate historical procedures, and populates the database with the demographic information and the candidate historical procedures and receives and handles individual events of the sensor platform and evaluates a status of the current procedure based upon the individual events.

Although the invention is illustrated and described herein as embodied in systems and methods for compound motor action potential monitoring with neuromodulation of the pelvis and other body regions, it is, nevertheless, not intended to be limited to the details shown because various modifications and structural changes may be made therein without departing from the spirit of the systems and methods and within the scope and range of equivalents of the claims. Additionally, well-known elements of exemplary embodiments will not be described in detail or will be omitted so as not to obscure the relevant details of the systems and methods.

Additional advantages and other features characteristic of the systems and methods will be set forth in the detailed description that follows and may be apparent from the detailed description or may be learned by practice of exemplary embodiments of the systems and methods. Still other advantages of the systems and methods may be realized by any of the instrumentalities, methods, or combinations particularly pointed out in the claims.

Other features that are considered as characteristic for the systems and methods are set forth in the appended claims. As required, detailed embodiments are disclosed herein; however, it is to be understood that the disclosed embodiments are merely exemplary of the systems and methods, which can be embodied in various forms. Therefore, specific structural and functional details disclosed herein are not to be interpreted as limiting, but merely as a basis for the claims and as a representative basis for teaching one of ordinary skill in the art to variously employ the systems and methods in virtually any appropriately detailed structure. Further, the terms and phrases used herein are not intended to be limiting; but rather, to provide an understandable description of the systems and methods. While the specification concludes with claims defining the features of the systems and methods that are regarded as novel, it is believed that the systems and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present systems and methods. Advantages of embodiments of the systems and methods will be apparent from the following detailed description of the exemplary embodiments thereof, which description should be considered in conjunction with the accompanying drawings in which:

FIG. 1 is a circuit diagram of an exemplary embodiment of a primary input of an electromyography muscle sensor;

FIG. 2 is a circuit diagram of an exemplary embodiment of an amplification circuit of an electromyography muscle sensor;

FIG. 3 is a circuit diagram of an exemplary embodiment of a rectification circuit of an electromyography muscle sensor;

FIG. 4 is a circuit diagram of an exemplary embodiment of a smoothing circuit of an electromyography muscle sensor;

FIG. 5 is a circuit diagram of an exemplary embodiment of a publication circuit of an electromyography muscle sensor;

FIG. 6 is a block diagram of an exemplary embodiment of a user portion of an electromyography muscle sensing device;

DETAILED DESCRIPTION OF THE INVENTION

Figure 7:
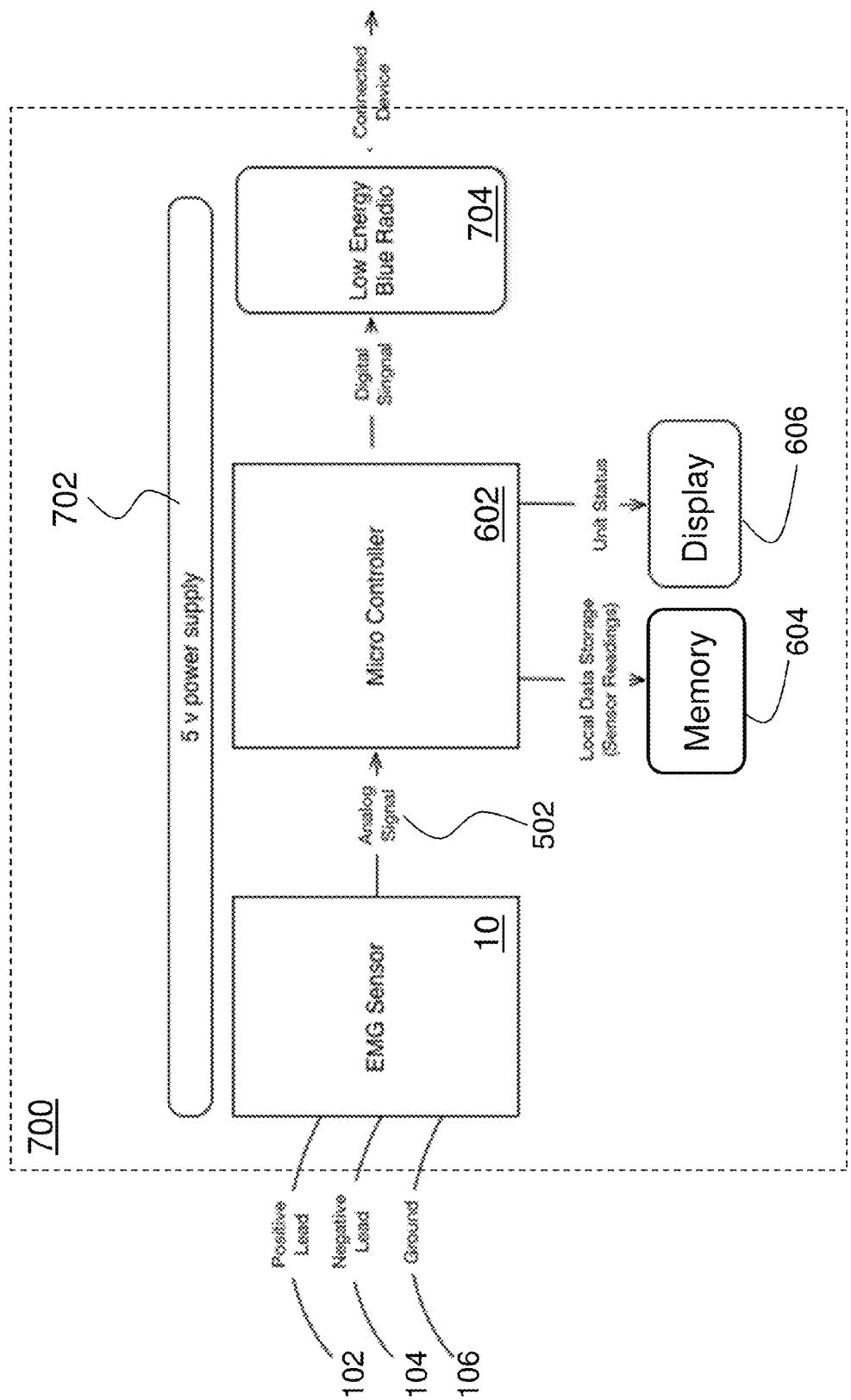
FIG. 7 is a block diagram of an exemplary embodiment of a user portion of an electromyography muscle sensing device.

As required, detailed embodiments of the present invention are disclosed herein; however, it is to be understood that the disclosed embodiments are merely exemplary of the systems and methods, which can be embodied in various forms. Therefore, specific structural and functional details disclosed herein are not to be interpreted as limiting, but merely as a basis for the claims and as a representative basis for teaching one skilled in the art to variously employ the systems and methods in virtually any appropriately detailed structure. Further, the terms and phrases used herein are not intended to be limiting; but rather, to provide an understandable description of the systems and methods. While the specification concludes with claims defining the features of the systems and methods that are regarded as novel, it is believed that the systems and methods will be better understood from a consideration of the following description in conjunction with the drawing figures, in which like reference numerals are carried forward.

Alternate embodiments may be devised without departing from the spirit or the scope of the systems and methods. Additionally, well-known elements of exemplary embodiments of the systems and methods will not be described in detail or will be omitted so as not to obscure the relevant details of the systems and methods.

Before the systems and methods are disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

It will be appreciated that embodiments described herein may be comprised of one or more conventional processors and unique stored program instructions that control the one or more processors to implement, in conjunction with certain non-processor circuits and other elements, some, most, or all of the functions of the devices described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system. A "program," "software," "application," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments of the systems and methods. These systems and methods include an electromyography muscle sensing device or EMG device 1 having an electromyography muscle sensor 10 associated with a microcontroller 602, described in further detail below. In an exemplary embodiment, the electromyography muscle sensing device 1 includes sending and return electrodes (which can be concentric), a grounding pad or grounding electrode, a display monitor (which can be a laptop, a smart phone, an iPad, or the like), cables or radio frequency sending and receiving units, and software.

The output of the sensor 10 is amplified, rectified, and smoothed to produce a signal that is able to work with the analog-to-digital converter either of the microcontroller 602 or separate from the microcontroller 602 but communicating with it. FIGS. 1 to 5 illustrate processing of the signal within the sensor 10. FIG. 1 illustrates a primary input 100 of the sensor 10 comprising three electrodes: positive 102; negative 104; and ground 106. First, a raw measurement of the current passing between the electrodes 102, 104 is made. The measurement is amplified, as shown in FIG. 2, by an amplification circuit 200, e.g., an AD8226 integrated circuit. Next, the measurement is rectified. FIG. 3 illustrates a rectification circuit 300 with a rectified output 302. The signal at the rectified output 302 is smoothed to remove line noise, for example, with a smoothing circuit 400 shown in FIG. 4, and produces a smoothed output signal 402. This smoothed output signal 402 is amplified, for example, with a publication circuit 500 shown in FIG. 5 and is published at an output signal 502. This output signal 502 returns an analogic value in volts (read 0-1023 by an analog-to-digital converter ("ADC")) to represent an electromyogram ("EMG") waveform. A manual potentiometer 504 is shown in this exemplary embodiment to strengthen or weaken the EMG value. In another exemplary embodiment, the microcontroller 602 can replace the manual device and digitally set the resistance, e.g., through commands by the user.

FIG. 6 is a diagrammatic representation of the sensor 10 and FIG. 7 is an expanded block circuit diagram of a user portion 700 of the electromyography muscle sensing device 1 with the sensor 10 and its various circuit components 100, 200, 300, 400, 500. Associated with the sensor 10 is a microcontroller 602. The microcontroller 602 can be part of the sensor 10 or separate from the sensor 10. Three contact points of the sensor 10 are represented in FIG. 6 as the three positive 102, negative 104, and ground 106 electrodes. The output signal 502 of the EMG sensor 10 is input to the microcontroller 602, which is a small system on a board computing device. The microcontroller 602 is powered by a power supply 702, for example, by an internal 5 v lithium battery, and can use a memory 604 for non-volatile storage, for example, a micro SD card. To display information to a user, a display 606 shows to the user various states, for example, a current status of the electromyography muscle sensing device 1 and an EMG raw value. The analog-to-digital converter receives the analog output signal 502 and converts it to a digital value. The frequency at which the value is sampled is controlled by the microcontroller 602. Each value received from the sensor 10 is stored in the memory 604 with associated values, including, e.g., date, time, and session identifier.

The electromyography muscle sensing device 1 is available in both a hardwired or connected configuration and a radiofrequency or wireless configuration to allow for maximum flexibility and accommodate constraints of individual practices. In an exemplary embodiment, the communications device 704 is wireless (e.g., a low energy Bluetooth 4.0 radio) that can communicate information from the microcontroller 602 to an external evaluation device, such as a laptop, desktop, tablet, smart phone, or other such devices, for post-processing and analysis. In this regard, the microcontroller 602 is able to receive configuration commands and to transmit EMG sensors values through the communications device 704.

A variety of user-directed settings and default settings can be overridden and modified. The following are exemplary specifications for the EMG device 1. Regarding the filter, there are settings for gain, high cut, and low cut. Examples of these filter setting include a gain of 100 microvolts/division, a high cut of 1,000 microvolts/division, and a low cut of 10 microvolts/division. A trigger threshold sensitivity can also be set to, for example, 20 microvolts as a default with available deviations in 10 microvolt increments. A time base can include both a live window and a trigger window. For example, a live window sweep speed can be 75 milliseconds/division and a trigger window (single waveform view) can be 10 milliseconds/division. The device can also have a selective audio filter in which "in use" is a default setting with an option to deactivate.

Figure 8:
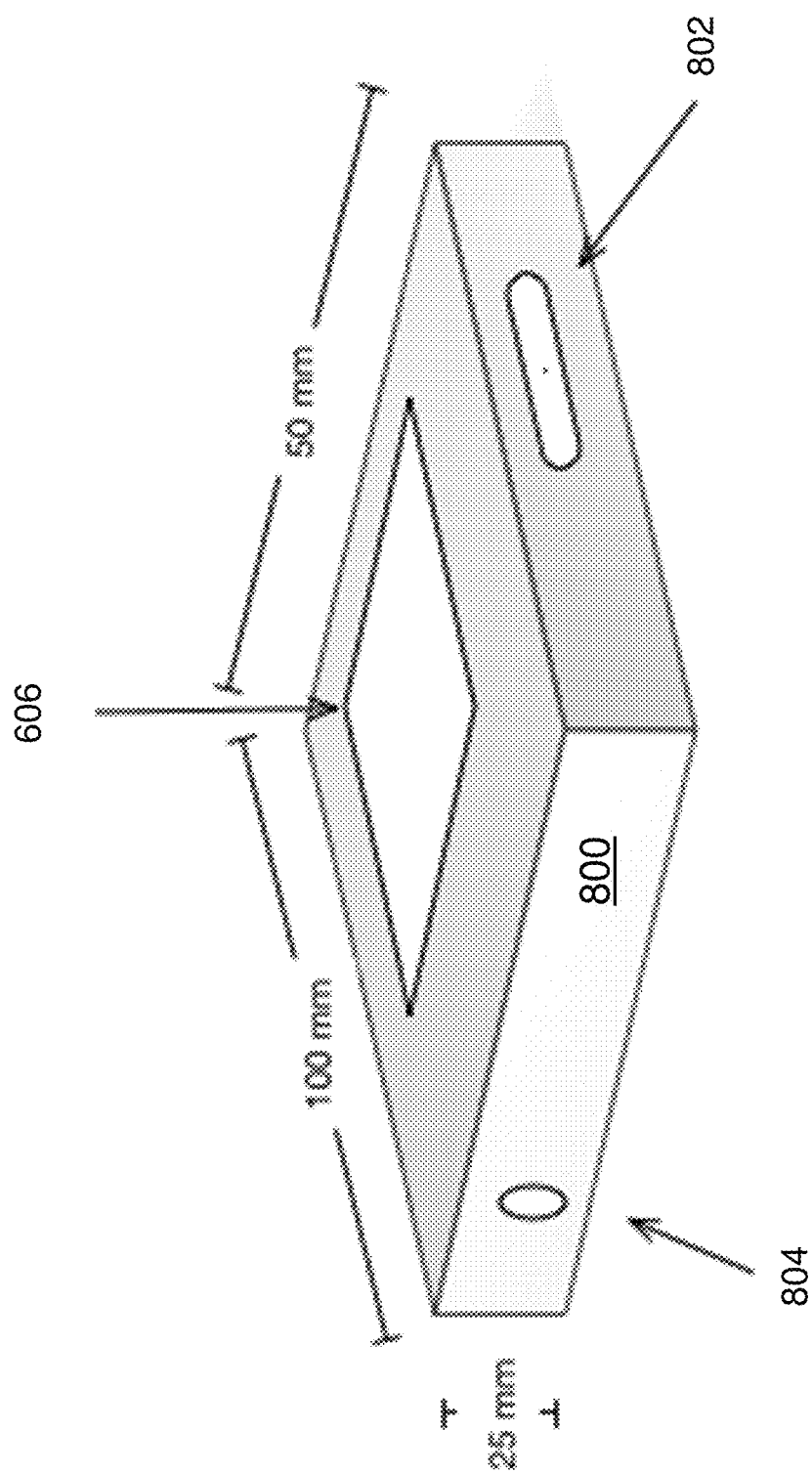
FIG. 8 is a perspective view of an exemplary embodiment of a form factor for a user portion of an electromyography muscle sensing device.

One exemplary embodiment of an external form factor 800 for the EMG sensor 10 is shown in FIG. 8. The form factor 800 is a handheld, streamlined unit and is similar in size and appearance to a typical hand-held device or "smart phone." The display 606 can be, e.g., a 30 mm OLED screen. Removable storage can be provided through a port 802 that, for example, is a micro SD slot. Connectivity of the electrodes 102, 104, 106 can be provided, for example, through a non-illustrated three-wire cable that connects to a port 804 (e.g., a 3.5 mm cable port). In this configuration, the overall size of the form factor 800 can be small. For example, the form factor 800 can be 100 mm wide, 50 mm high, and 25 mm thick.

Figure 9:
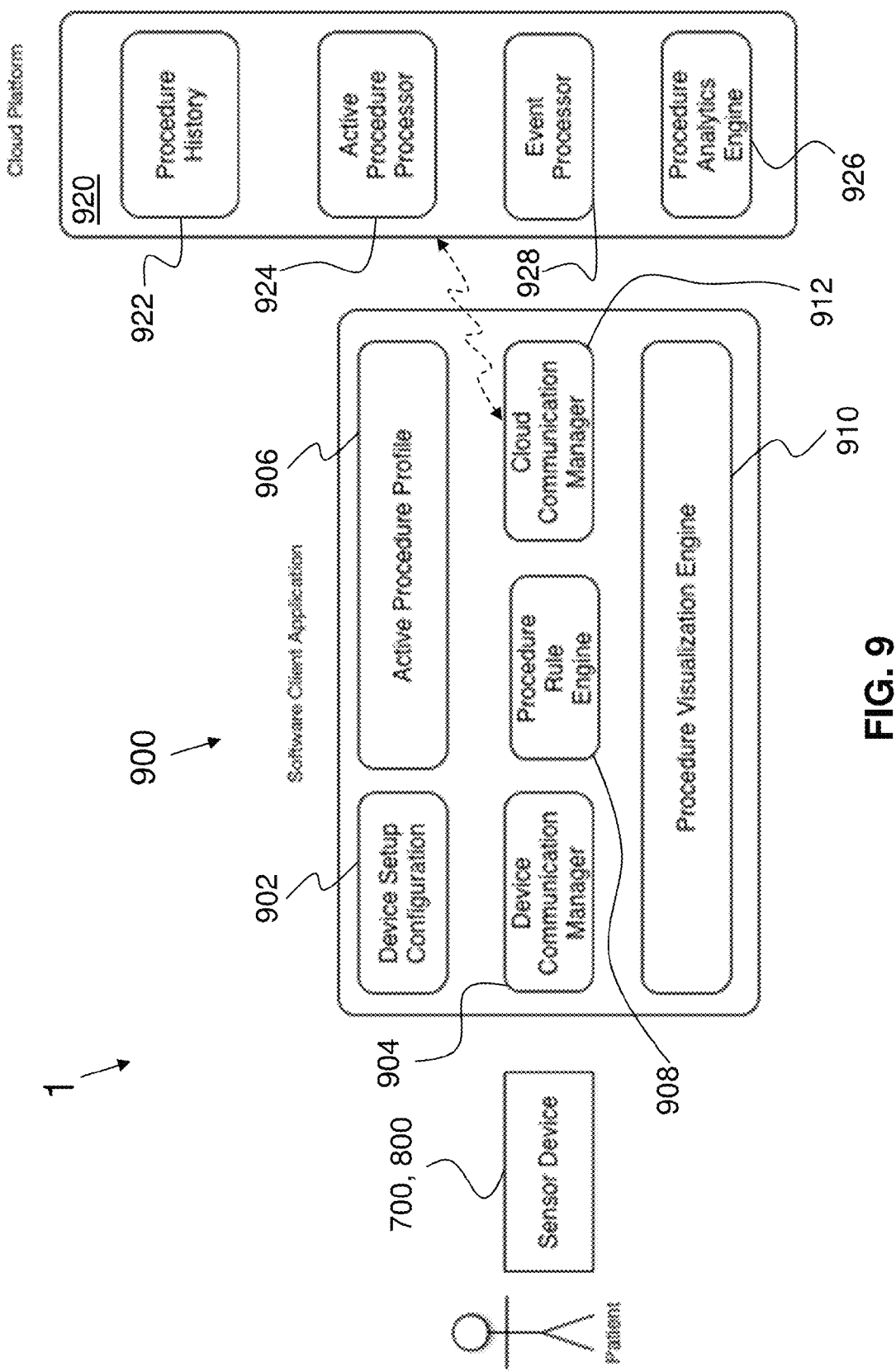
FIG. 9 is a block diagram of an electromyography muscle sensing device.
Figure 10:
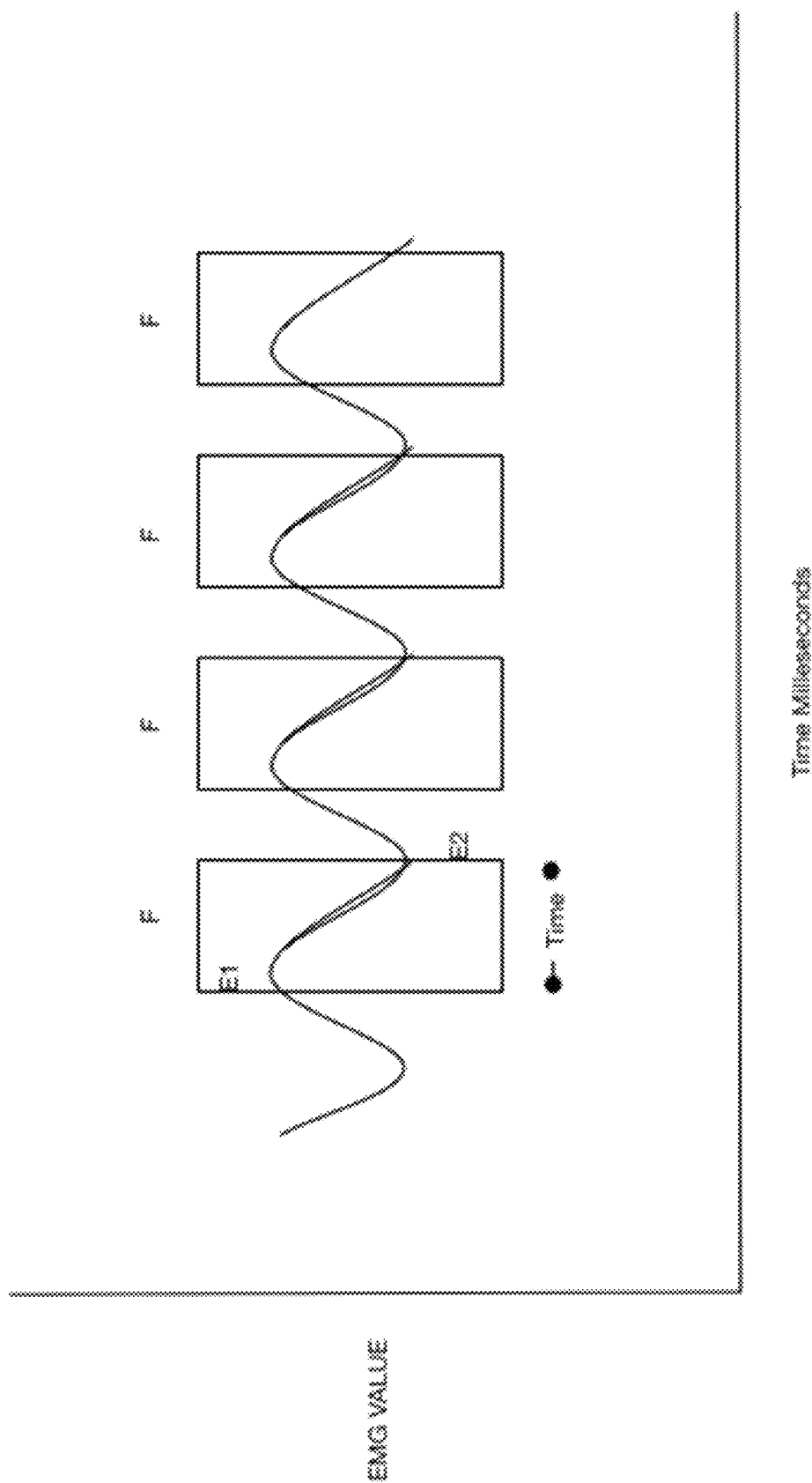
FIG. 10 is a graph of a CMAP wave form of an electromyography muscle sensing device.

FIG. 9 diagrammatically represents a client software application 900 used to receive, visualize, and interpret the values from the user portion 700 of the electromyography muscle sensing device 1. Additionally, the software application 900 is used to configure settings on the user portion 700. The application 900 is broken into several modules. Each module is responsible for specific activities. A Device Setup Configuration Module 902 controls the settings of the sensor 10. Some of the settings that are controlled include voltage, signal gain, sample frequency, and amplitude. The processor 602 records the configuration settings for each CMAP session in the memory 604, for example, for permanent or temporary storage. A Communication Manager Module 904 provides the directives for using the communications device 704, e.g., the Bluetooth capability, to communicate to and from the user portion 700. A secret encrypted token is passed to the user portion 700 from outside devices to authorize communications. Each command sent to the user portion 700 is recorded in the memory 604. An Active Procedure Profile Module 906 maintains the record of the current CMAP procedure being performed. This Active Procedure Profile Module 906 includes, for example, the patient's demographic information, the procedure's duration, and EMG event data. A Procedure Rule Engine 908 is the software module that determines if CMAP is being achieved based upon current EMG event data and past procedure outcomes. One example formula for determining CMAP is configurable but is based upon the following:

$$\text{Delta EMG} = \text{ABS}(E1-E2);$$

where: time between E1 and E2 is T milliseconds. The Delta EMG value is in a valid numeric range and occurs with a defined frequency. FIG. 10 graphically represents achieving CMAP, the waveform being smooth as CMAP is achieved. The high and low value indication (E1 and E2) over time represents the patient's electrical response to electrical stimulation. The graph of FIG. 10 give the surgeon positive or negative visual cues as the waveform matches the CMAP characteristics from other procedures (which matching is described in further detail below). One example of a positive visual cue is that the waveform takes on a green color. Likewise, one example of a negative visual cue is that the waveform takes on a red color. The software within the sensor platform 700 filters out noise of the system that is associated with electrical artifact, patient movement, and extraneous muscle activity, for example. This filtering is important because it allows the user/surgeon to interpret a "pure" nerve response; accordingly, the system graphs only relevant data on the display. (This being significantly different from the prior art technology that only graphs raw data and only does so from a single, current patient. This lack of filtering, as stated above, requires the user/surgeon to have significant expertise and intuition or premonition to identify when CMAP actually is achieved.

The values of Delta EMG, Time and Frequency are set to defaults and are also gathered from other previously successful procedures with a similar profile, whether from the same patient or from different patients. A Procedure Visualization Engine 910 is the software component that graphically maps out a value of the output signal 502 of the EMG sensor 10 and visually communicates to the user (e.g., surgeon) whether or not CMAP is being achieved. CMAP can be indicated by sound, by lights and/or graphics on the display, and/or by tactile measures, such as vibration of the form factor 800. Finally, a Cloud Communication Manager 912 is the software module that sends (dashed line) event and procedure data to a cloud-based data gathering and analysis platform 920, such as an off-site server. The data that is sent out is used in real-time to validate that CMAP has been achieved and to record instances of achieving CMAP so that future uses can be compared to an ever-increasing data set within that offsite database. If desired, every time a CMAP procedure is undertaken, the electromyography muscle sensing device 1 can store the session data in the cloud and the user can tag that data as achieving either a successful or unsuccessful CMAP. In this way, with live access to the system's database, the electromyography muscle sensing device 1 is able to compare in real time a current procedure with all other procedures and is able to match the patient being examined to other patients with similar demographics.

The electromyography muscle-sensing device 1 has both receiving and sending capabilities to create a printer friendly report directly or to interface with electronic medical record systems and provide a virtual report. The memory 604 of the electromyography muscle-sensing device 1 is capable of filing a patient specific record that will be accessible for future use when needed.

As mentioned above, previous and previously successful procedures are utilized by the sensor platform 700 to make the determination of achieving CMAP. To assist each sensor platform 700 with this data analysis, a separate data platform is provided and utilized. So that users from all over the world can access past data, in an exemplary embodiment, the data analysis platform is a cloud-based or cloud platform 920 with which every different one of many sensor platforms 700 communicate and exchange data. The cloud platform 920 centrally organizes and stores data from each and/or all use of the sensor platforms 700. The cloud platform 920 of the electromyography muscle sensing device 1, in particular, can be a centralized computer system (such as a server connected to the Internet) that maintains a history of each clinical procedure. Detailed demographics, individual events, and procedure outcomes are used to provide real-time feedback to surgeons and historical analytics to improve procedure efficacy. A Procedure History Module 922 permanently stores all data received. Data is stored in a redundant and secure manner that is compliant with all privacy laws. An Active Procedure Processing Module 924 maintains each active procedure session. The Active Procedure Processing Module 924 authenticates and authorizes the surgeon to use the user portion 700 and records demographic information. The Active Procedure Processing Module 924 also coordinates interaction with the other software modules in the platform 920. The Active Procedure Processing Module 924 uses the entered demographic information to identify candidate historical procedures and populate a database associated with an Analytics Engine 926. The Active Procedure Processing Module 924 communicates in real time with the Procedure History Module 922 all results of the surgical procedure being undertaken. An Event Processing Module 928 receives and handles individual events of each of the one or more user portions 700 available to different physicians/surgeons/users. Events are persistently stored and handed off to the Analytics Engine 926 for evaluation of current procedure status.

The Analytics Engine 926 uses industry machine-learning techniques to predict the outcome of active procedures. The Analytics Engine 926 compares current event data with previously identified similar past procedures to determine if the event data correlates with a future successful outcome. In one exemplary embodiment, the Analytics Engine 926 uses Fourier analysis to compare the CMAP waveforms from one or more or all previous procedures. While Fourier analysis is known in the art, one example of processing signals with this method can be found at the Fourier Series description by Wolfram Mathworld at mathworld.wolfram.com.

The CMAP waveform produced is analyzed using Fourier or other time series analysis and is transformed or decomposed into a "signature." A neural network or other classification algorithm is trained to classify the decomposed signature or the waveform directly as either CMAP or non-CMAP. Alternatively, standard regression methods can provide a likelihood of CMAP having been achieved (e.g., the algorithm returns a score between 0 and 1, where 1 indicates complete CMAP). Training the classification or regression algorithm will build and obtain training data composed of the waveforms and their associated classifications (or likelihoods, for regression analysis), validated by a human expert or other "gold standard" method.

Figure 13:
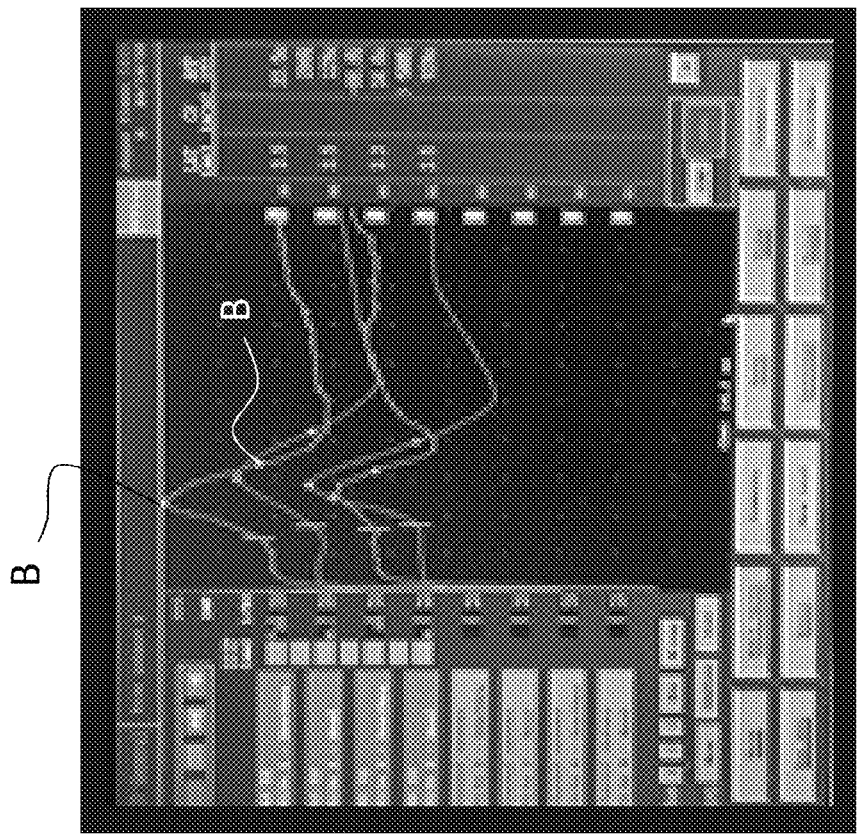
FIG. 13 is a photograph of a prior art display of a CMAP device.
Figure 12:
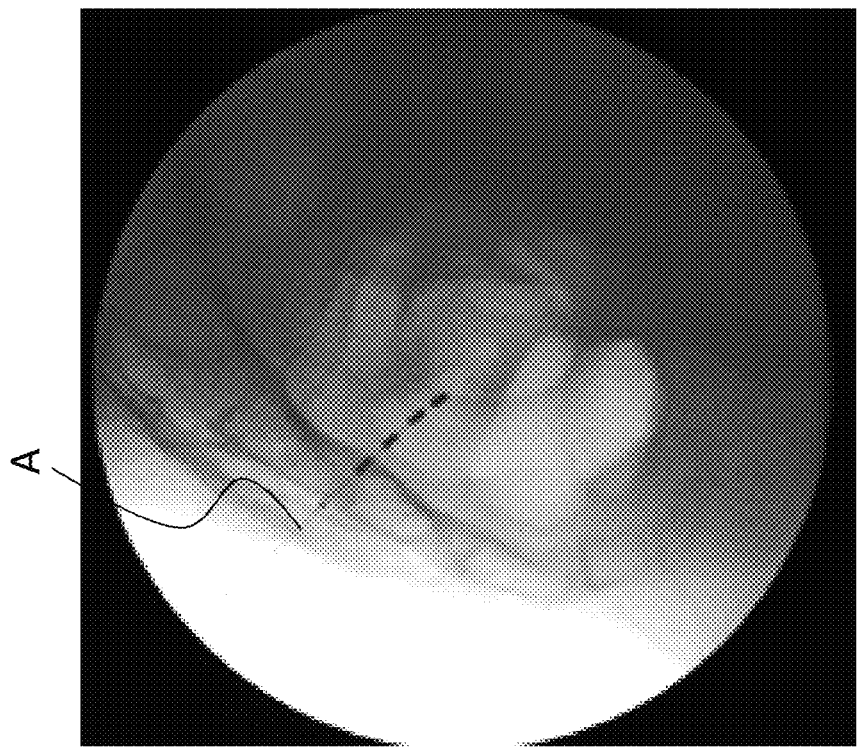
FIG. 12 is a radiograph of placement of a prior art stimulation lead.

As set forth above, prior art systems only allow a surgeon to see a waveform such as that shown in FIG. 13 and to use his/her intuition to determine whether CMAP is achieved. The devices, systems, and processes here, in contrast, allow the surgeon to determine immediately if CMAP is achieved without having to use guesswork. Regarding the form of indicators that are visible to user, the exemplary embodiment described above has the electromyography muscle sensing device 1 turns the screen green in color when CMAP is achieved and has the screen remain red in color if CMAP is not achieved. In this way, anyone can tell whether CMAP is achieved. Alternatively, the color-coded display changes in intensity (e.g., a red to green color change) with increasing intensity of a CMAP response, the red screen indicating to the user lack of CMAP response and a green display indicating strong CMAP response. Along with the color display, various graphic confirmatory signal can be provided, e.g., a "thumbs up/thumbs down" or other indicator symbols. Actual CMAP output signal tracing with triggering markers is also an available display option (e.g., FIG. 10), which the user can choose to activate and visualize if desired. Threshold measurements, latency and other parameters of nerve conduction are available through advanced user software packages.

In an exemplary embodiment, the device 1 provides both visual and auditory prompts and feedback (positive and negative) regarding nerve response to stimulation. This neuro-based guidance allows for optimal and consistent application of neuromodulation technology and also facilitate recording of testing.

A form of the display 606 is dependent upon the physical platform. Even though the user portion 700 is envisioned to be a separate handheld device accessing a cloud-based database, it can also be resident on a laptop, a smart phone, a tablet, or the like. In such embodiments, the physical display is the one already present on the device being used.

It is envisioned that the user portion 700 is reusable over a lifetime that includes many different patient monitoring procedures. Some of the components for use with the electromyography muscle sensing device 1, however, are disposable. For example, a disposable electrode/ground receiving headbox is an interface for the test electrodes and ground that interface with the user portion 700. An exemplary embodiment of a grounding block is a non-sterile small (approx 1") contact body. The head box is a single channel interface large enough to easily handle but small enough to fit under a surgical drape and, as set forth above, connects to the user portion 700 that is either radio frequency controlled or hard wired connected by a cable. The cable will be a 20-22 gauge wire that will be 6-10 feet in length. Also the various electrodes can be disposable. The electrode can be 27- to 30-gauge concentric needles 1.5 cm in length connected by a 22-gauge wire to the headbox (although a surface patch is also envisioned). The electrodes are single use materials individually packaged in sterile containers. Sponge electrodes are also disposable. Such sponges take the form of an inert sponge matrix having a wire embedded therein, the wire receiving summated signals from the surface of the sponge. This configuration may be used within an orifice, such as a rectum, a vagina, a urethra, a mouth, and a nose. These sponges will be packaged as single use sterile items.

As set forth herein, the user portion 700 of the electromyography muscle sensing device 1 can be a program that is resident on a smart phone or a tablet (or the like) and the electrodes can interface with any of the various input/output subsystems of such devices (e.g., USB connections). The program can be purchased through an online application store as well as be available through major platforms/vendors. The application interfaces with Electronic Medical Record ("EMR") systems and allows both data storage and retrieval. In a hard wired configuration of the electromyography muscle sensing device 1, the monitoring equipment can be a headblock that connects, for example, via a standard cell phone charging port.

Figure 11:
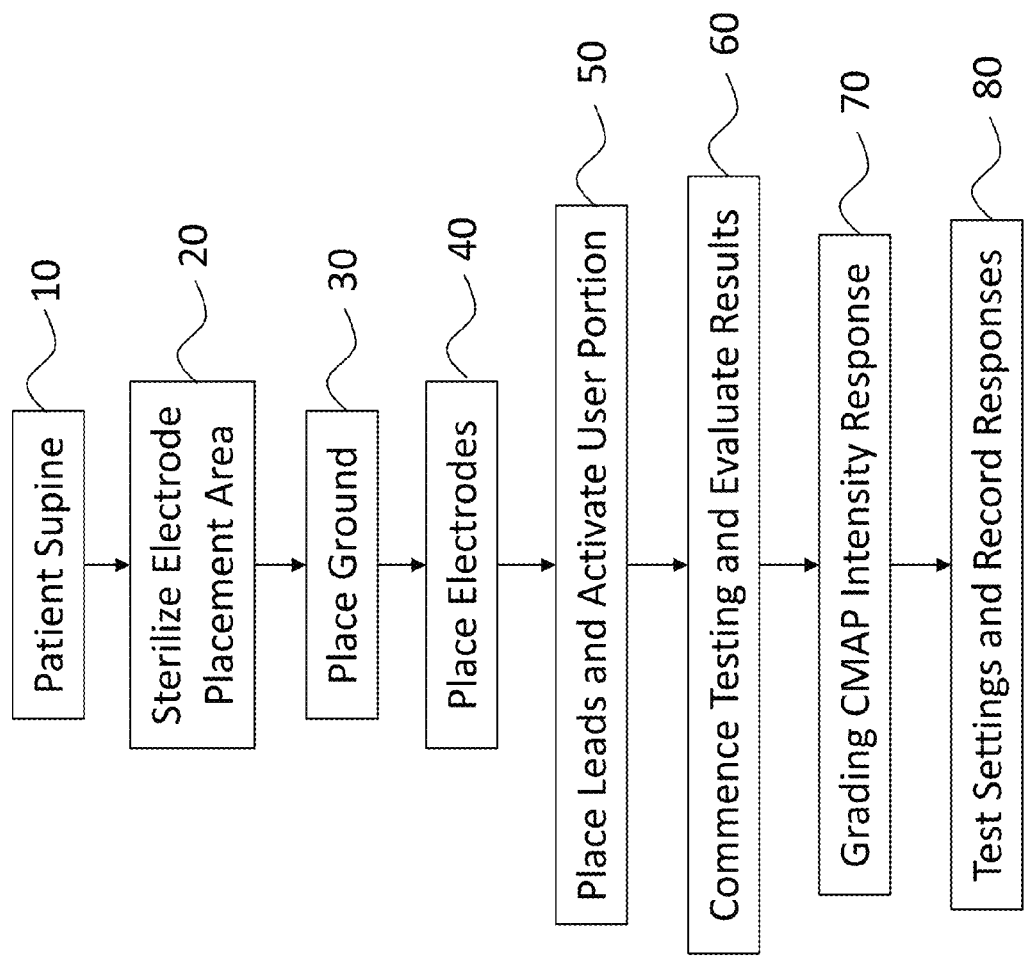
FIG. 11 is a flow chart of an exemplary embodiment of a method for conducting electromyography muscle sensing.

An exemplary method for operating the EMG device 1 is described below with regard to the flow chart of FIG. 11. This is an exemplary process used to help understand one specific use and the methods are not limited thereto and can include other applicable scenarios. This method can be applied to both operative scenarios and in-office evaluations. In step 10, the patient is placed in a supine position on a bed/table. The area of the anus is cleansed and prepped in step 20. A grounding needle/patch is applied on the patient's hip and is taped in place in step 30. In a needle electrode embodiment, in step 40, right and left sided perianal electrodes are inserted at 3 and 9 o'clock into the external anal sphincter of the patient. In a sponge electrode embodiment, a rectal sponge electrode is placed within the anus by the surgeon in step 40. In step 50, leads of the electrodes are plugged into a headblock (either cabled or wireless) and the user portion 700 is activated. The user, in step 60, sets up the EMG device 1 by, for example, verifying a baseline on free running EMG, looking for noise, and adjusting the system's filters. Before starting the procedure, the user ensures that the patient remains quiet without excess muscle activity. In step 70, the CMAP testing procedure is commenced and testing results are evaluated. An intensity of the CMAP response is graded in step 80 based upon auditory and/or visual feedback from the EMG device 1. In step 90, a predetermined array of stimulatory cathode/anode settings are tested and responses are recorded. If appropriate responses are noted, then the testing procedure is complete. Finally, the electrodes/sponge and grounding lead are removed.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The phrase "at least one of A and B" is used herein and/or in the following claims, where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables.

The foregoing description and accompanying drawings illustrate the principles, exemplary embodiments, and modes of operation of the systems and methods. However, the systems and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems and methods as defined by the following claims.

What is claimed is:

1. An electromyography muscle sensing system, comprising:
   a sensor platform having:
      an electromyography muscle sensor having:
         sensing electrodes with patient contacts at which electrical energy is at least one of measured and supplied; and
         a signal processing circuit electrically connected to the sensing electrodes and having a sensor output;
      an analog-to-digital converter electrically connected to the sensor output and having a digital output at which is supplied a signal representing an electromyogram waveform;
      a memory;
      a communications device sending output data from the sensor platform and receiving input data into the sensor platform;

a display displaying information to a user to indicate at least one of a status of the sensor platform and an indication of CMAP presence or absence; and a microcontroller electrically connected to the sensor, the analog-to-digital converter, the memory, the display, and the communications device, the microcontroller:

receiving from the digital output the signal and storing at least a portion of the signal in the memory;

maintaining a record of a current procedure being performed by the sensor platform;

providing communication directives to the communications device to transmit in real-time at least portions of the record to and/or from the sensor platform;

determining if CMAP is being achieved in the current procedure; and providing at the display at least one of the status of the sensor platform and the indication of CMAP presence or absence; and a cloud-based data analysis and storage platform communicatively connected at least to the communications device of the sensor platform to receive the output data from the sensor platform and to send the input data to the sensor platform, the cloud-based data analysis and storage platform:

having a database;

centrally organizing and storing the output data from the sensor platform in the database;

maintaining a history of each procedure of the sensor platform in the database;

analyzing the stored output data and the history to define stored output data of a successful CMAP outcome;

storing the output data in the database and asking the user to tag that data as achieving one of a successful CMAP and an unsuccessful CMAP every time a CMAP procedure is undertaken with the sensor platform;

predicting an outcome of the current procedure by comparing at least a portion of the output data in the current procedure with output data in the database to determine if the portion of the current output data correlates with the stored output data of the successful CMAP outcome; and communicating in real time the outcome of the current procedure.

2. The electromyography muscle sensing system according to claim 1, wherein at least one of the electromyography muscle sensor and the communications device of the sensor platform is a wireless handheld sensor platform.

3. The electromyography muscle sensing system according to claim 1, wherein the sensor platform is one of a laptop, a smart phone, and a tablet.

4. The electromyography muscle sensing system according to claim 1, wherein the sensor platform is a plurality of sensor platforms.

5. The electromyography muscle sensing system according to claim 1, wherein the sensing electrodes comprise a positive electrode, a negative electrode, and a ground electrode.

6. The electromyography muscle sensing system according to claim 1, wherein the signal processing circuit includes:

an amplification circuit having an input connected to at least one of the electrodes and a first amplification output;

a rectification circuit connected to the first amplification output of the amplification circuit having a rectified output at which is provided a rectified signal;

a smoothing circuit connected to the rectified output, smoothing the rectified signal, and having a smoothed output; and a publication circuit amplifying the smoothed output and publishing the output signal.

7. The electromyography muscle sensing system according to claim 1, wherein a voltage of the output signal supplied to the analog-to-digital converter represents the electromyogram waveform.

8. The electromyography muscle sensing system according to claim 1, wherein:

the signal includes values of at least one of date, time, and session identifier; and the microcontroller stores the values in the memory.

9. The electromyography muscle sensing system according to claim 1, wherein the communications device is a wireless radio.

10. The electromyography muscle sensing system according to claim 1, wherein the communications device is a Bluetooth radio.

11. The electromyography muscle sensing system according to claim 1, wherein the signal processing circuit includes at least one of:

a filter having settings for gain, high cut, and low cut;

a trigger threshold sensitivity;

a time base with a trigger window; and a selective audio filter.

12. The electromyography muscle sensing system according to claim 1, wherein the user and default settings of the sensor include at least one of voltage, signal gain, sample frequency, and amplitude.

13. The electromyography muscle sensing system according to claim 1, wherein the record of the current procedure includes a patient's demographic information, a procedure duration, and EMG event data.

14. The electromyography muscle sensing system according to claim 1, wherein CMAP is achieved according to the formula Delta EMG=ABS(E1−E2), where a time between E1 and E2 is in milliseconds and EMG is a value of the digital output.

15. The electromyography muscle sensing system according to claim 1, wherein a graphical mapping is indicated at the display by at least one of sound, lights, graphics, and tactile measures.

16. The electromyography muscle sensing system according to claim 1, wherein the cloud platform is a centralized computer server connected to the Internet.

17. The electromyography muscle sensing system according to claim 1, wherein the cloud platform stores data stored securely to comply with health information privacy laws.

18. The electromyography muscle sensing system according to claim 1, wherein the microcontroller is programmed to:

receive from the digital output the signal at a sampling rate frequency and store the sampled digital output in the memory;

control user and default settings of the sensor;

record the settings in the memory for each procedure conducted by the user of the sensor platform; and map a value of the sensor output and communicate to the user whether or not CMAP is being achieved.

19. The electromyography muscle sensing system according to claim 1, wherein the cloud-based data analysis and storage platform:
  authenticates and authorizes use of the sensor platform and, upon authorization, records demographic information of the patient, identifies candidate historical procedures, and populates the database with the demographic information and the candidate historical procedures; and
  receives and handles individual events of the sensor platform and evaluates a status of the current procedure based upon the individual events.

20. An electromyography muscle sensing system, comprising:
  a sensor platform having:
    an electromyography muscle sensor having:
      sensing electrodes with patient contacts at which electrical energy is at least one of measured and supplied; and
      a signal processing circuit electrically connected to the sensing electrodes and having a sensor output;
    an analog-to-digital converter electrically connected to the sensor output and having a digital output at which is supplied a signal representing an electromyogram waveform;
    a memory;
    a communications device sending output data from the sensor platform and receiving input data into the sensor platform;
    a display displaying information to a user to indicate at least one of a status of the sensor platform and an indication of CMAP presence or absence; and
    a microcontroller electrically connected to the sensor, the analog-to-digital converter, the memory, the display, and the communications device, the microcontroller:
      receiving from the digital output the signal and storing at least a portion of the signal in the memory;
      maintaining a record of a current procedure being performed by the sensor platform;
      providing communication directives to the communications device to transmit in real-time at least portions of the record to and/or from the sensor platform;
      determining if CMAP is being achieved in the current procedure; and
      providing at the display at least one of the status of the sensor platform and the indication of CMAP presence or absence; and
  a cloud-based data analysis and storage platform communicatively connected at least to the communications device of the sensor platform to receive the output data from the sensor platform and to send the input data to the sensor platform, the cloud-based data analysis and storage platform:
    having a database;
    centrally organizing and storing the output data from the sensor platform in the database;
    maintaining a history of each procedure of the sensor platform in the database;
    analyzing the stored output data and the history to define stored output data of a successful CMAP outcome;
    authenticating and authorizing use of the sensor platform and, upon authorization, recording demographic information of the patient, identifying candidate historical procedures, and populating the database with the demographic information and the candidate historical procedures;
    receiving and handling individual events of the sensor platform and evaluating a status of the current procedure based upon the individual events;
    predicting an outcome of the current procedure by comparing at least a portion of the output data in the current procedure with output data in the database to determine if the portion of the current output data correlates with the stored output data of the successful CMAP outcome; and
    communicating in real time the outcome of the current procedure.

21. The electromyography muscle sensing system according to claim 20, wherein the sensor platform is a wireless handheld sensor platform.

22. The electromyography muscle sensing system according to claim 20, wherein the sensor platform is one of a laptop, a smart phone, and a tablet.

23. The electromyography muscle sensing system according to claim 20, wherein the sensor platform is a plurality of sensor platforms.

24. The electromyography muscle sensing system according to claim 20, wherein the sensing electrodes comprise a positive electrode, a negative electrode, and a ground electrode.

25. The electromyography muscle sensing system according to claim 20, wherein the signal processing circuit includes:
  an amplification circuit having an input connected to at least one of the electrodes and a first amplification output;
  a rectification circuit connected to the first amplification output of the amplification circuit having a rectified output at which is provided a rectified signal;
  a smoothing circuit connected to the rectified output, smoothing the rectified signal, and having a smoothed output; and
  a publication circuit amplifying the smoothed output and publishing the output signal.

26. The electromyography muscle sensing system according to claim 20, wherein a voltage of the output signal supplied to the analog-to-digital converter represents the electromyogram waveform.

27. The electromyography muscle sensing system according to claim 20, wherein:
  the signal includes values of at least one of date, time, and session identifier; and
  the microcontroller stores the values in the memory.

28. The electromyography muscle sensing system according to claim 20, wherein the communications device is a wireless radio.

29. The electromyography muscle sensing system according to claim 20, wherein the communications device is a Bluetooth radio.

30. The electromyography muscle sensing system according to claim 20, wherein the signal processing circuit includes at least one of:
  a filter having settings for gain, high cut, and low cut;
  a trigger threshold sensitivity;
  a time base with a trigger window; and
  a selective audio filter.

31. The electromyography muscle sensing system according to claim 20, wherein the user and default settings of the sensor include at least one of voltage, signal gain, sample frequency, and amplitude.

32. The electromyography muscle sensing system according to claim 20, wherein the record of the current procedure includes a patient's demographic information, a procedure duration, and EMG event data.

33. The electromyography muscle sensing system according to claim 20, wherein CMAP is achieved according to the formula Delta EMG=ABS(E1−E2), where a time between E1 and E2 is in milliseconds and EMG is a value of the digital output.

34. The electromyography muscle sensing system according to claim 20, wherein a graphical mapping is indicated at the display by at least one of sound, lights, graphics, and tactile measures.

35. The electromyography muscle sensing system according to claim 20, wherein the cloud platform is a centralized computer server connected to the Internet.

36. The electromyography muscle sensing system according to claim 20, wherein the cloud platform stores data stored securely to comply with health information privacy laws.

37. The electromyography muscle sensing system according to claim 20, wherein the microcontroller is programmed to:

receive from the digital output the signal at a sampling rate frequency and store the sampled digital output in the memory;

control user and default settings of the sensor;

record the settings in the memory for each procedure conducted by the user of the sensor platform; and map a value of the sensor output and communicate to the user whether or not CMAP is being achieved.

38. The electromyography muscle sensing system according to claim 20, wherein, every time a CMAP procedure is undertaken with the sensor platform, the cloud-based data analysis and storage platform stores the output data in the database and asks the user to tag that data as achieving one of a successful CMAP and an unsuccessful CMAP.

* * * * *